United States Patent
Reif

[11] Patent Number: 6,113,632
[45] Date of Patent: Sep. 5, 2000

[54] SUTURE RING FOR HEART VALVE PROSTHESIS

[75] Inventor: Thomas H. Reif, Vero Beach, Fla.

[73] Assignee: Republic Medical Products Inc., Vero Beach, Fla.

[21] Appl. No.: 09/161,268

[22] Filed: Sep. 26, 1998

Related U.S. Application Data

[62] Division of application No. 29/076,617, Sep. 3, 1997.

[51] Int. Cl.[7] .................................................. A61F 2/24
[52] U.S. Cl. ............................................... 623/2.4
[58] Field of Search ............................. 623/2, 2.38, 2.39, 623/2.4

[56] References Cited

U.S. PATENT DOCUMENTS

| | | | |
|---|---|---|---|
| 3,997,923 | 12/1976 | Possis | 623/2 |
| 4,790,843 | 12/1988 | Carpentier et al. | 623/2 |
| 5,178,633 | 1/1993 | Peters | 623/2 |
| 5,855,603 | 1/1999 | Reif | 623/2 |

Primary Examiner—David H. Willse
Assistant Examiner—Alvin Stewart
Attorney, Agent, or Firm—Albert H. Reuther, Esq.

[57] ABSTRACT

A heart valve stiffening ring of this disclosure includes a split ring that allows assembly over a channel-shaped heart-valve-orifice-forming angular heart valve body, with the split ring having an outer peripheral tapered thread, which allows adjustment of pressure between the split ring and the orifice-forming annular body. A solid ring or nut has complementary tapered threads to mate with the outer peripheral tapered thread of the split ring and is adjustable for tightening of interfit thereof to bring about correct pressure for desired tightening effect with a moment of inertia in bending of the outer channel to make the orifice stronger so that orifice outer diameter thereof can be a maximum value. The angle of taper is substantially 3 degrees with respect to the center line. This heart valve stiffening ring can be employed in place of a heart valve locking ring of U.S. Design Pat. No. 376,206-Reif issued Dec. 3, 1996. Improvement of the present design includes a major feature or crux that the split ring and solid ring or nut both have complementary threads that fit together and using the flanges of the channel configuration used therewith.

12 Claims, 2 Drawing Sheets

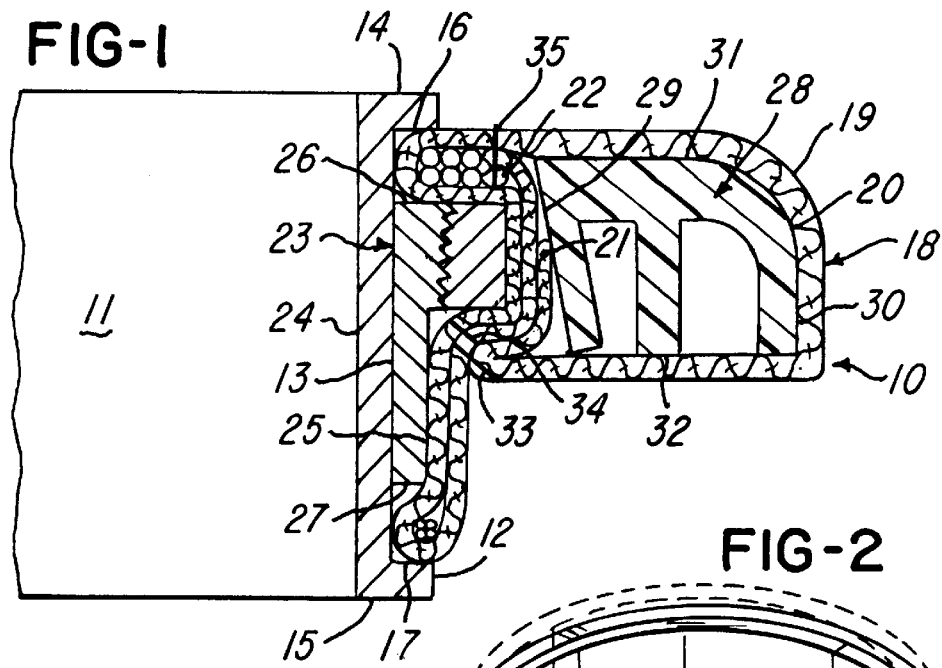
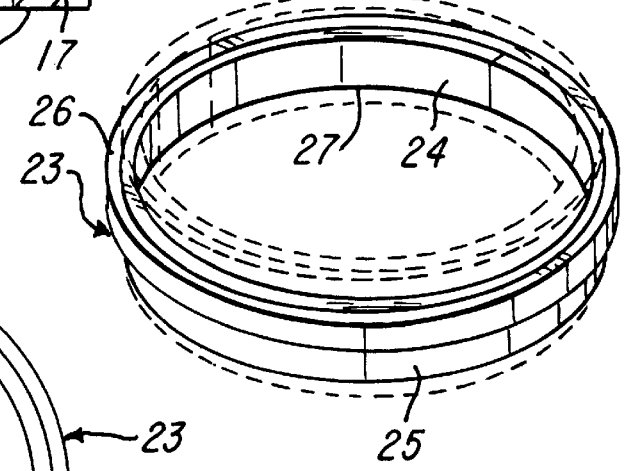
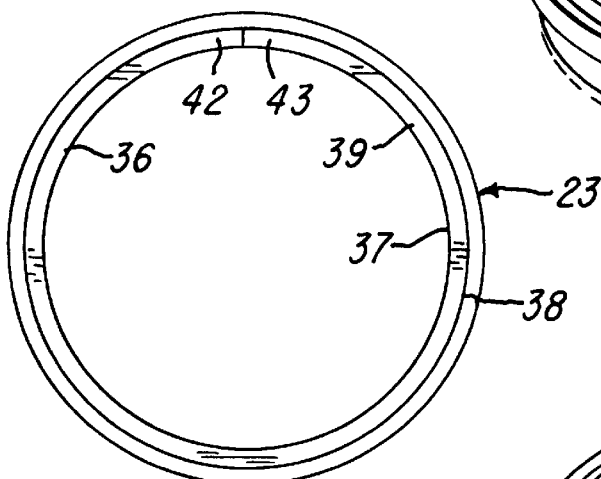
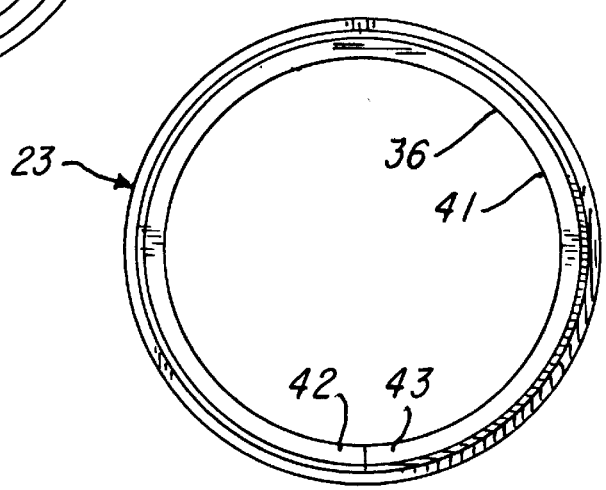

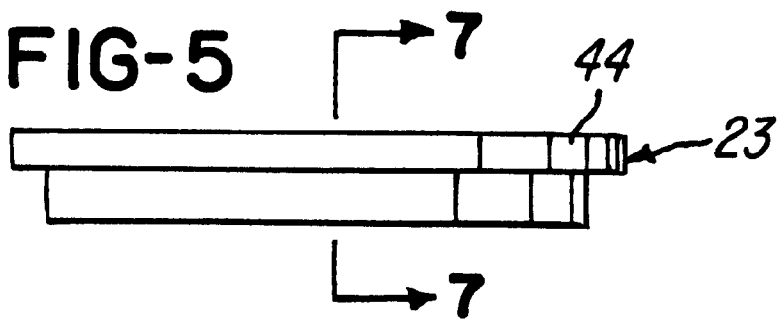
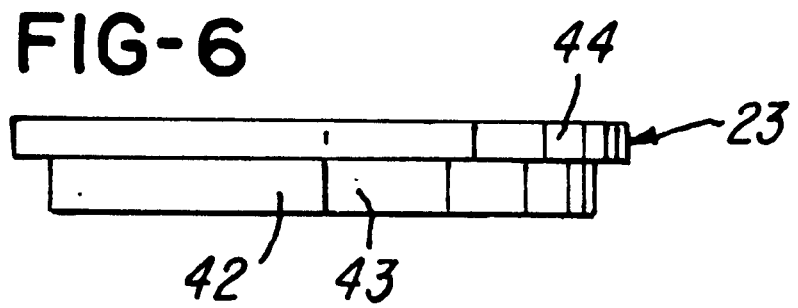
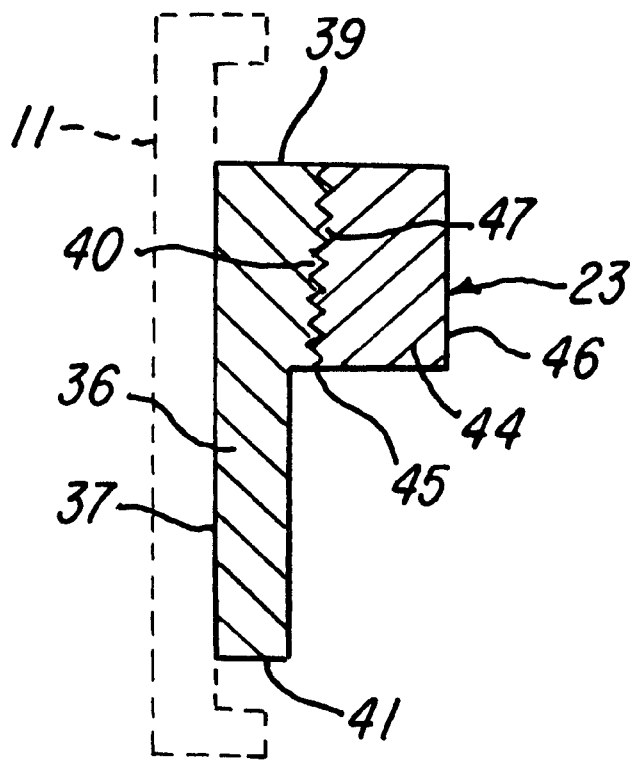

SUTURE RING FOR HEART VALVE PROSTHESIS

This is a divisional application based upon co-pending Design application Ser. No. 29/076,617-Reif filed Sep. 3, 1997, based thereon, and entitled Heart Valve Stiffening Ring, respectively.

BACKGROUND OF THE INVENTION

1. Field of the Invention

The present invention relates to a heart valve prostheses, and more particularly to suture rings for supporting heart valve prostheses.

2. Description of the Prior Art

There are two types of heart valve prostheses, biological and mechanical. The medical indications for heart valve replacement are the same for both types. Examples include rheumatic heart disease, congenital anomalies, and myocardial infarction.

Unidirectional flow is the primary function of the heart valve prostheses. This is usually accomplished by fashioning rigid or flexible leaflets, free to articulate within certain limitations, within an annular shaped frame, frequently referred to as an orifice ring. The restrained motion of these leaflets causes the flow to be essentially unidirectional, mimicking the natural function of the native heart valves.

While the features of the present invention can be used in either biological or mechanical valves, for purposes of facilitating explanation thereof the present prior art disclosure dissertation will be limited to mechanical valves such as disclosed in U.S. Pat. No. 4,276,658-Hansen dated Jul. 7, 1981; U.S. Pat. No. 4,689,046-Bokros dated Aug. 25, 1987; and U.S. Pat. No. 4,950,287-Reif dated Nov. 12, 1991. The leaflets of mechanical valves are usually constructed of pyrolytic carbon or a composite of pyrolytic carbon and a substrate, such as graphite or titanium. The leaflets are typically constrained within an orifice ring also constructed of the same materials. In most cases, the orifice ring is deformed in order to insert the leaflets during manufacture. Therefore, it is desirable for the orifice ring to be somewhat compliant. If the orifice ring is too stiff, a significant percentage may be permanently damaged during the insertion process. It is also desirable to maximize the internal diameter of the orifice ring, since this reduces the pressure gradient through the valve, reducing the work that the heart must perform during each stroke.

The orifice ring with the inserted leaflets is often referred to as a subassembly. The subassembly is usually attached to the heart by using a biocompatible fabric material, such as knitted polyester. The fabric material is usually purchased or fashioned into a tubular configuration. There are several methods of fixation of the fabric material to the subassembly. One possibility is disclosed in U.S. Pat. No. 3,718,969-Anderson dated Jan. 1, 1974, where the subassembly is placed inside of the fabric tube and a heat shrinkable plastic band is placed around the outside diameter of the fabric tube. The fabric material is then folded into an annular configuration often referred to as the suture ring. Sometimes annular shaped filler rings, often constructed of polytetrafluoroethylene or silicon elastomer, are inserted within the folded portion of the fabric tube in order to make the suture ring larger and/or more compliant. It is desirable that a suture ring be rotatable relative to the subassembly, as this feature greatly facilitates implantation into the heart. The use of a heat shrinkable plastic band is one method of achieving rotatability.

Significant forces are applied to the suture ring during both the surgical implantation of the heart valve and during its service life in the body. These forces are transmitted to the leaflets via the orifice ring. It is possible, therefore, to damage the subassembly both during and after implantation. The use of a heat shrinkable plastic band requires that the orifice ring have substantial stiffness. This makes the insertion of the leaflets more difficult and reduces the internal diameter of the orifice ring, both of which are undesirable. Since pyrolytic carbon is a preferred material for the orifice ring, and since it is much more compliant than metal (about 7.5 times more compliant than steel, and about 3.8 times more compliant than titanium), it is apparent that both of these problems can be overcome by using a metal stiffening ring around the outside diameter of the subassembly.

U.S. Pat. No. 5,071,431-Sauter et al. dated Dec. 10, 1991 uses a continuous metal stiffening ring. The inside diameter of the stiffening ring is in direct proximity to the outside diameter of the subassembly, but not in direct contact with it. The inside diameter of the fabric tube is in direct contact with the outside diameter of the stiffening ring and continuous metal fastener bands are used at the proximal and distal ends of the stiffening ring in order to fix the fabric tube to the stiffening ring. This stiffening ring of U.S. Pat. No. 5,071,431-Sauter et al. uses a metal split ring as a means to prevent the stiffening ring from disengaging from the subassembly and to provide some control over the rotatability of the subassembly within the suture ring. In practice, the assignee of U.S. Pat. No. 5,071,431-Sauter et al., with this stiffening ring, uses a metal wire for this purpose. The outside diameter of the orifice has a small groove, the inside diameter of the stiffening ring has a similar small groove, and the metal wire passes within this potential resultant groove space. Therefore, the outside diameter of the orifice ring is constrained by the stiffening ring only over the small contact area from the wire. The disadvantage to this method of constraint is that it requires the orifice ring to be thicker than it would be if the constraint were to be applied over a larger portion of the external diameter of the orifice ring. This is because the leaflets transfer significant loads to the orifice ring, when the leaflets are in the closed position. For the same loading conditions from the leaflets, the larger the area of constraint on the outside diameter of the orifice ring, the lower the stress in the orifice ring. Increasing the thickness of the orifice ring results in a decrease in the inside diameter of the orifice ring, which is an undesirable effect.

Similar arguments can be used to discount the effectiveness of the continuous metal stiffening ring disclosed in U.S. Pat. No. 5,397,348-Campbell et al. dated Mar. 14, 1995. In this disclosure, the stiffening ring contacts the subassembly only along the first and second axial ends of the stiffening ring, because the patentees, Campbell et al., claim that an even larger gap should exist between the outside diameter of the stiffening ring and the outside diameter of the subassembly.

U.S. Pat. No. 5,178,633-Peters dated Jan. 12, 1993 discloses another concept where a continuous metal band is heat shrinked onto the outside diameter of the subassembly. As disclosed by Dr. Joseph E. Shigley in his text, *Mechanical Engineering Design*, 3 Ed., McGraw-Hill Book Co., New York, 1977, pp. 63–69, shrink fits cause significant radial and circumferential stresses in the inner member (orifice ring after shrink fit), and significant stresses can be induced in constrained bodies undergoing heating (orifice ring during shrink fit process). The disadvantage to this method of constraint is that it too requires the orifice ring be thicker than it would if the constraint were to be applied without the press fit.

U.S. Pat. No. 4,863,460-Magladry dated Sep. 5, 1989 discloses a continuous metal stiffening ring covered by fabric, which can be electromagnetically deformed inwardly, clamping the suture ring to the subassembly. U.S. Pat. No. 4,743,253-Magladry dated May 10, 1988 is similar to the U.S. Pat. No. 4,863,460-Magladry disclosure, but utilizes a split ring. Both of these concepts present problems with manufacturing, particularly potential damage to the subassembly, acceptable stiffness characteristics, and biocompatability.

In summary, there are several disadvantages to the current prior art design configurations of suture rings in heart valve prostheses. Some designs are inadequate because they require metal orifice rings instead of the preferred material, pyrolytic carbon. Other designs fail to maximize the internal diameter of the orifice ring, even while utilizing pyrolytic carbon. Further, some designs subject the pyrolytic orifice rings to undesirable stresses and potential damage during manufacture.

SUMMARY OF THE INVENTION

A heart valve prosthesis is disclosed which has a compliant orifice ring, housing one or more leaflet(s). The outside diameter of the orifice ring has a channel shape. The inside diameter of a split metal ring contacts a portion of the outside diameter of the orifice ring. One of the ends of the outside diameter of the split ring is threaded. A solid metal ring, with a threaded inside diameter attaches, via this thread, to the threaded portion of the outside diameter of the split ring. The threads are tapered so as to allow adjustment of the contact pressure between the inside diameter of the split ring and the outside diameter of the orifice ring. The stiffening ring is here defined as the assembled split ring and solid ring. The outside diameter of the stiffening ring is contoured to increase its moment of inertia in bending, therefore, increasing its stiffness. A fabric tube covers parts of the channel portion of the outside diameter of the orifice ring and the outside diameter of the stiffening ring.

With the foregoing in mind, it is an object of the present invention to provide a heart valve prosthesis, which is rotatable. It is also an object of the present invention to provide a heart valve prosthesis with an orifice ring having a relatively large internal diameter.

Another object of the present invention is to provide a heart valve prosthesis that is easily and rapidly manufactured. A further object of the present invention is to provide a heart valve prosthesis whereby the contact pressure between the orifice ring and the stiffening ring can be adjusted. This controls the contact stresses in the mating components.

Other objects and advantages of the present invention will become apparent from the following detailed description, taken with reference to the accompanying drawings.

BRIEF DESCRIPTION OF THE DRAWINGS

FIG. 1 is a cross-sectional view of the suture ring attached to the orifice ring;

FIG. 2 is a top perspective view of the assembled stiffening ring;

FIG. 3 is a top plan view of the assembled stiffening ring of FIG. 2;

FIG. 4 is a bottom plan view of the assembled stiffening ring of FIG. 2;

FIG. 5 is a side elevational view of the assembled stiffening ring of FIG. 2;

FIG. 6 is an elevational view of the assembled stiffening ring of FIG. 2; and

FIG. 7 is a cross-sectional view, greatly enlarged, taken on line 7—7 of FIG. 5 with a cross-section of the channel-shaped orifice ring shown in phantom lines.

DESCRIPTION OF PREFERRED EMBODIMENTS

The following description is of the best mode presently contemplated for practicing the invention. This description is not to be taken in a limiting sense, but is made for the purpose of describing the general principles of the invention. The scope of the invention should be determined with reference to the claims. The preferred embodiment of the present invention will now be described with reference to the accompanying drawings. In the drawings, like numerals will be used to designate like parts throughout.

FIG. 1 depicts a cross-sectional view of the suture ring 10, attached to the orifice ring 11. The orifice ring 11 may house leaflets as disclosed in U.S. Pat. No. 4,950,287-Reif dated Nov. 12, 1991. The orifice ring has an outer circumferential surface 12 with a substantial annular groove 13. The orifice ring 11 has a first axial end 14 and a second axial end 15. Flanged surfaces 16 and 17 are formed at the intersection of the outer circumferential surface 12 and the annular groove 13.

The fabric tube 18 has an external surface 19 and an internal surface 20. The fabric tube 18 also has a first axial end 21 and a second axial end 22. The external surface 19 of the fabric tube 18 directly contacts the flanged surfaces 16 and 17 and the annular groove 13 of the orifice ring 11.

The stiffening ring 23 has an internal circumferential surface 24, an external circumferential surface 25, a first axial end 26, and a second axial end 27. The radial thickness of the stiffening ring is greater at the first axial end 26 than it is at the second axial end 27. The fabric tube 18 is folded such that the external surface 18 of the fabric tube 19 directly contacts the external circumferential surface 25 of the stiffening ring 23.

The filler ring 28 is of basic annular configuration with internal circumferential surface 29, external circumferential surface 30, first axial end 31, and second axial end 32. The filler ring 28 is arranged so that the internal surface 29 thereof contacts the folded over internal surface 20 of the fabric tube 18 at the first axial end 21 of the fabric tube 18. The first axial end 31, the second axial end 32, and the external surface 30 of the filler ring 28 all contact the internal surface 20 of the fabric tube 18. Suture lines 33 and 34 fix the first axial end 21 of the fabric tube 18, while suture line 35 fixes the second axial end 22 of the fabric tube 18, such that the suture ring 10 remains intact.

Mode of Operation

FIG. 2 depicts a top perspective view of the stiffening ring 23. The stiffening ring 23 is constructed from two pieces. The first piece is a split ring 36. It is first machined into an annular configuration with the appropriate inside surface diameter 37 and outside surface diameter 38. The first axial end 39 of the split ring 36 is threaded with a male tapered thread 40. The second axial end 41 of the split ring 36 is left unthreaded. The split ring 36 is the split from its annular configuration by a method such as wire electrical discharge. This process causes the formation of a first radial end 42 and a second radial end 43. The radial ends 42 and 43 of the split ring 36 are shown more clearly in FIG. 3, a top plan view of the stiffening ring, and in FIG. 4, a bottom plan view of the stiffening ring. The radial ends 42 and 43 are also shown in FIGS. 5 and 6, side elevational and elevational views of the stiffening ring 23, respectively.

The second piece of the stiffening ring 23 is a solid ring 44. The solid ring 44 is first machined into an annular configuration with the appropriate inside surface diameter 45 and outside surface diameter 46. The inside surface of the solid ring 45 is then threaded with a female tapered thread 47. The male tapered thread 40 of the split ring 36 mates with the female tapered thread 47 of the solid ring. The male tapered thread 40 and the female tapered thread 47 are shown more clearly in FIG. 7, a cross-sectional view, detailed greatly enlarged of the stiffening ring 23.

The radial thickness of the first axial end 26 of the stiffening ring 23 is greater than it is at the second axial end 27. This increases the moment of inertia in bending of the stiffening ring 23. Such a configuration is more stiff than it would be if the entire stiffening ring 23 had the same radial thickness as the second axial end 27. Therefore, this increase in the moment of inertia in bending enables the use of a larger inside diameter of the orifice ring 11 (FIG. 1).

The present invention (FIG. 1) permits the use of an orifice ring 11 with a very thin radial thickness. This makes insertion of the leaflets safer and easier, since the orifice ring 11 is more compliant. It also increases the inside diameter of the orifice ring 11, which is highly desirable because of improved hemodynamics.

Assembly of the suture ring 10 (FIG. 1) is also facilitated by the use of a two-piece stiffening ring 23. The subassembly is made first (leaflets mounted in the orifice ring). The stiffening ring 23 is disassembled by removing (unthreading) the solid ring 44 from the split ring 36. The split ring 36 is then passed around the external surface 12 of the orifice ring 11. The split ring 36 is then released allowing contact between the inside surface 37 of the split ring 36 and the annular groove 13 of the orifice ring 11. The solid ring 44 is then passed over the external surface 12 of the orifice ring 11 and then threaded to the split ring 44. Care is taken to correctly mate the male tapered thread 40 of the split ring 36 and the female tapered thread 47 of the solid ring 44. The threaded connection is left loose. The stiffening ring 23 is positioned within the annular groove 13 of the orifice ring 11 and the threading mechanism is tightened. The fabric tube 18 is then folded as depicted in FIG. 1, the filler ring 28 is inserted, and the fabric tube 18 is fixed with suture lines 33–35.

The assembled heart valve prosthesis is rotatable; it provides for an orifice ring 11 having a relatively large internal diameter. It is easily and rapidly manufactured. Also, the contact pressure between the orifice ring 11 and the stiffening ring 23 can be readily adjusted.

In conclusion, suture ring for heart valve prosthesis of the present invention includes a heart valve stiffening ring having two parts, a split ring 36 and a solid ring 44, positioned relative to annular members including a heart valve subassembly and fabric tube respectively cloth wrapped around the heart valve stiffening ring as represented in FIG. 1 herewith. The filler ring 28 is an outer annular ring of plastic or fabric material adapted to be fitted concentrically around the metal stiffening ring per se of FIG. 1.

The present invention is, of course, in no way restricted to the specific disclosure of the specification and drawings, but also encompasses any modifications within the scope of the appended claims.

What I claim is:

1. A suture ring for a heart valve prosthesis which is rotatable comprising:

an orifice ring having a relatively large internal diameter;
a stiffening ring having an internal circumferential surface and an external circumferential surface, a first axial end and a second axial end, said stiffening ring having a radial thickness thereof that is greater at the first axial end than at the second axial end; a fabric tube folded such that an internal surface of the fabric tube directly contacts the external circumferential surface of the stiffening ring; and a filler ring of basic annular configuration with an internal circumferential surface, an external circumferential surface, a first axial end, and a second axial end, said filler ring being arranged so that the internal surface thereof contacts the fabric tube, a split ring being threaded with a male tapered thread, said stiffening ring being a solid ring first machined into an annular configuration with appropriate inside surface diameter and outside surface diameter, the inside surface of the solid ring being threaded with a female tapered thread, said male tapered thread of said split ring having a mating relationship with the female tapered thread of said solid ring.

2. A suture ring according to claim 1, with which the first axial end, the second axial end and the external surface of said filler ring all contact the external surface of the fabric tube.

3. A suture ring according to claim 2, in which at least one suture line fixes the first axial end of the fabric tube, one further suture line fixing the second axial end of the fabric tube so that the suture ring remains intact.

4. A suture ring according to claim 1, in which said stiffening ring is constructed including two pieces, a first piece thereof being a split ring first machined into an annular configuration with appropriate inside surface diameter and outside surface diameter, the first axial end of said split ring being threaded with a male tapered thread, the second axial end of said split ring being left unthreaded, said split ring being split from its annular configuration that causes formation of a first radial end and a second radial end.

5. A suture ring for a heart valve prosthesis which is rotatable comprising:

an orifice ring having a relatively large internal diameter;
a stiffening ring having an internal circumferential surface and an external circumferential, a first axial end and a second axial end, said stiffening ring having a radial thickness thereof that is greater at the first axial end than at the second axial end; a fabric tube folded such than an internal surface of the fabric tube directly contacts the external circumferential surface of the stiffening ring; and a filler ring of basic annular configuration with an internal circumferential surface, an external circumferential surface, a first axial end, a second axial end, said filler ring being arranged so that the internal surface thereof contacts the folded over internal surface of the fabric tube at the first axial end of the fabric tube, said stiffening ring being constructed including two pieces, a first piece thereof being a split ring first machined into an annular configuration with appropriate inside surface diameter and outside surface diameter, the first axial end of said split ring being threaded with a male tapered thread, the second axial end of said split ring being left unthreaded, said split ring being split from its annular configuration that causes formation of a first radial end and a second radial end, a second piece of said stiffening ring being a solid ring first machined into an annular configuration with appropriate inside surface diameter and outside surface diameter, an inside surface of the solid ring being threaded with a female tapered thread, said male tapered thread of said split ring having a mating relationship with the female tapered thread of said solid ring.

6. A suture ring according to claim 5, in which an increase of moment of inertia in bending of the stiffening ring results from the radial thickness of the first axial end of the stiffening ring being greater than that at the second axial end, such configuration being more stiff than if the stiffening ring in entirety had the same radial thickness as the second end, this increase in moment of inertia in bending enabling use of a larger inside diameter of the orifice ring.

7. A suture ring according to claim 6, in which a very thin radial thickness of the orifice ring is permitted therewith and the orifice ring is consequently more compliant making insertion of heart valve leaflets safer and easier and also increasing an inside diameter of the orifice ring, which is highly desirable because of improved hemodynamics.

8. An assembly of a suture ring for heart valve prosthesis, comprising a heart valve stiffening ring having two parts including a split ring and a solid ring positioned relative to annular members including a heart valve subassembly and fabric tube respectively cloth wrapped around the heart valve stiffening ring, and a filler ring which is an outer annular ring of material fitted concentrically around the stiffening ring of metal.

9. An assembly of the suture ring according to claim 8, in which the stiffening ring as a subassembly is disassembled by removing the solid ring from the split ring by unthreading therefrom, said split ring then passing around an external surface of an orifice ring with the split ring then being released allowing contact between an inside surface of the split ring and an annular groove of the orifice ring, the solid ring then being passed over an external surface of the orifice ring and then being threaded to said split ring.

10. An assembly of the suture ring according to claim 9, in which there is correctly mated relationship of the male tapered thread of the split ring and female tapered thread of the solid ring in a threaded connection that is left loose, the stiffening ring being positioned with the annular groove of the orifice ring, and then interfitting male and female threads are tightened, subsequently having a fabric tube folded therewith with the filler ring inserted and the fabric tube being fixed with suture lines.

11. An assembly of the suture ring according to claim 8, in which said outer annular ring is plastic material.

12. An assembly of the suture ring according to claim 8, in which said outer annular ring is fabric material.

* * * * *